United States Patent [19]

Barbic et al.

[11] Patent Number: 5,096,826

[45] Date of Patent: Mar. 17, 1992

[54] METHOD OF MEASURING SPECIFIC SURFACE AREA

[75] Inventors: Lenart Barbič, Most na Soči; Magda Godina, Anhovo, both of Yugoslavia

[73] Assignee: Salonit Anhovo, industrija gradbenega materiala, n.sol.o, Anhovo, Yugoslavia

[21] Appl. No.: 275,837

[22] Filed: Nov. 25, 1988

[30] Foreign Application Priority Data

Nov. 27, 1987 [YU] Yugoslavia ............................ 2164/87
Nov. 27, 1987 [YU] Yugoslavia ............................ 2165/87

[51] Int. Cl.$^5$ .......................................... G01N 24/00
[52] U.S. Cl. ........................................ 436/5; 324/317; 436/173
[58] Field of Search ............... 422/68.1; 436/5, 173; 73/863.23, 152; 324/316, 317

[56] References Cited

U.S. PATENT DOCUMENTS

| | | | |
|---|---|---|---|
| 4,413,512 | 11/1983 | Zemanek | 73/152 |
| 4,435,977 | 3/1984 | Gournay | 364/422 |
| 4,467,642 | 8/1984 | Givens | 324/362 |

FOREIGN PATENT DOCUMENTS 1221562  3/1986  U.S.S.R. .

OTHER PUBLICATIONS

Barbic et al., Determination of Surface Development in Cement Pastes by Nuclear Magnetic Resonance, Jour. of Amer. Ceramic Society, vol. 65, No. 1, 1982, pp. 25–31.

Barbic, L.; Kocuvan, Ivan; Blinc, R., Determination of Surface Development in Cement Pastes by Nuclear Magnetic Resonance, Journal of the American Ceramic Society, vol. 65, No. 1, pp. 25–31, 1982.

Kumar, J.; Fatt, I.; Saraf, D. N., Nuclear Magnetic Relaxation Time of Water in a Porous Medium with Heterogeneous Surface Wettability, Journal of Applied Physics, vol. 40, No. 10, Sep. 1969, abstract.

Pearson, R. M.: Ream, L. R.; Adams, J. Q., NMR Studies of Aluminum Oxide, ACS, Abs. of Papers, 194th Meeting, New Orleans 1987, Div. of Inorg. Chem. Abs 393, American Chemical Society, abstract.

Brown, Yorke J., Improved Measurement of the Surface Area . . . Journal of Low Temp. Physics, vol. 60, No. 3–4, Aug. 1985, abstract.

Davis, P. J., Gallegos, D. P.; Smith, D. M., Rapid Surface Area Determination via NMR spin . . . Lattice Relaxation Measurements Powder Technology., Nov. 1987, vol. 53, No. 1, pp. 39–47, abstract.

Susic, Milenko V.; Vucelic Dusan R.; Pausak, Steven V.; Nuclear Magnetic Resonance Method for the Determination of Specific Surface Area, Journal of Physical Chemistry, vol. 73, No. 6, pp. 1975–1984, 1969.

Schreiber, L. B.; Vaughan, R. W., Nuclear Magnetic Resonance Investigation of High Surface Area Silica–Aluminas, Journal of Catalysis, vol. 40, pp. 226–235, 1975.

*Primary Examiner*—Richard V. Fisher
*Assistant Examiner*—John J. Bruckner
*Attorney, Agent, or Firm*—Pollock, Vande Sande & Priddy

[57] ABSTRACT

A method for determining the specific surface of a porous or a powdery substance includes measuring the spin-lattice relaxation rate of impregnating agent protons, in which the impregnating agent is removed from a specimen of the impregnated, examined substance at a pressure below the saturated vapor pressure of the impregnating agent. The effective spin-lattice relaxation time $T_{1,ef}$ of impregnating agent protons is measured at several impregnating agent levels of the specimen and the specific surface of the examined substance is determined according to a given equation.

6 Claims, 2 Drawing Sheets

METHOD OF MEASURING SPECIFIC SURFACE AREA

BACKGROUND OF THE INVENTION

1. Field of the Invention

The invention relates to a method and to an apparatus for determining the specific surface $s_{NMR}$ of a porous or a powdery substance by measuring the spin-lattice relaxation rate of exchanging protons of an impregnating agent by means of nuclear magnetic resonance.

The specific surface $s_{NMR}$ determined by the present invention method corresponds to the surface of outwards open pores per mass unit of the examined substance, which surface has been moistened by the impregnating agent. Consequently, the surface $s_{NMR}$ is equal to the surface of a monomolecular impregnating agent layer still existing in the specimen of the examined substance after removing the impregnating agent for a long time. This removal of the impregnating agent is accomplished by evaporation at a pressure below the saturated vapor pressure of the impregnating agent at a given temperature. This is of great importance since it makes the method of the invention for an order of magnitude faster than the known method. Therefore this method appears appropriate for the investigation of diverse surface processes, such as the hydratization of cement. A measuring vessel with the specimen is connected to a vacuum pump system and is placed into a thermostatically controlled probe of a NMR spectrometer.

2. Description of the Prior Art

There has been known a method for determining the specific surface of a porous or a powdery substance by measuring the spin-lattice relaxation rate of impregnating agent protons, as described in the article "The determination of Surface Development in Cement Pastes by Nuclear Magnetic Resonance", J. Am. Cer. Soc., 65 (1982), 25-31.

A specimen is prepared from the examined substance (mass m), which substance is impregnated by an impregnating agent (mass $m_i$) to an impregnation level $m_i/m$. The impregnating agent should neither chemically react with the examined substance not get occluded by it. As impregnating agents there are used for example, $H_2O$, $C_2H_5OH$, $C_6H_{12}$, $C_3H_7OH$ and other liquids. The specimen of a porous substance is prepared by impregnating the substance in a vacuum ($m_i/m \approx 0.1$), the specimen of a powdery substance, however, is prepared by kneading a paste after it has been impregnated ($m_i/m \approx 0.1 \div 0.5$). The specimen is placed into a test cylinder, which is preferably punctured in order that the exhalation of the impregnating agent may be intensified. The effective relaxation time $T_{1,ef}$ of impregnating agent protons is measured with a NMR spectrometer with coherent pulses at several impregnation levels $m_i/m$ lying within a linerly shaped part of a curve $T_{1,ef}^{-1}$ vs. $(m_1/m)^{-1}$ and at very low impregnation levels $m_i/m$ after a long time exhalation when the effective relaxation time $T_{1,ef}$ is approaching the relaxation time $T_{1b}$ of the protons of the impregnating agent molecules, which remained in a monomolecular layer adsorbed to the pore surface.

The specific surface $s_{NMR}$ determined by nuclear magnetic resonance is expressed by the slope of the linearly shaped part of the curve $T_{1,ef}^{-1}$ vs. $(m_i/m)^{-1}$:

$$s_{NMR} = A \frac{T_{1b} \Delta\left(\frac{1}{T_{1,ef}}\right)}{\Delta\left(\frac{m_i}{m}\right) - 1},$$

with $A = \frac{N_L}{M_i} S_1$.

$S_1$ means the surface covered by one molecule of the impregnating agent with the molar weight $M_i$ and $N_L$ is the Loschmidt number.

The impregnating agent is removed from the specimen by exhalation, which makes this process rather lengthy. The exhaled vapor is condensed on the test cylinder walls, which makes impossible a precise measurement of the mass $m_i$ of the impregnation agent still remaining within the specimen and being non-uniformly distributed therein. It is a disadvantage of the described method that it is not suitable when the proton relaxation rate of the impregnating agent "in situ" is not negligible with respect to the proton relaxation rate of the impregnating agent within the adsorbed layer, since in this case the expected accuracy cannot be achieved.

SUMMARY OF THE INVENTION

The object of this invention is to provide a method which will make possible a fast removal of the impregnating agent from the specimen of the impregnated examined substance and a more uniform impregnating agent distribution within the specimen volume, which will prevent the impregnating agent vapors from condensing on the test cylinder walls and thus increase the accuracy of the proposed method, and which will make possible determining of the specific surface of a porous or a powdery substance, in which the relaxation rate of the protons of the impregnating agent "in situ" has to be taken into account additionally to the relaxation rate of the protons within the adsorbed layer.

Another object of the present invention is to create an apparatus to perform the proposed method, which apparatus will make possible a fast removal of the impregnating agent from the impregnated specimen during a continuous measuring of the NMR signal intensity without allowing specimen lumps to be stripped off.

Specific embodiments of the present invention will be presented in the following detailed description in conjunction with the accompanying drawings.

DETAILED DESCRIPTION OF THE PREFERRED EMBODIMENTS

Figure 1:
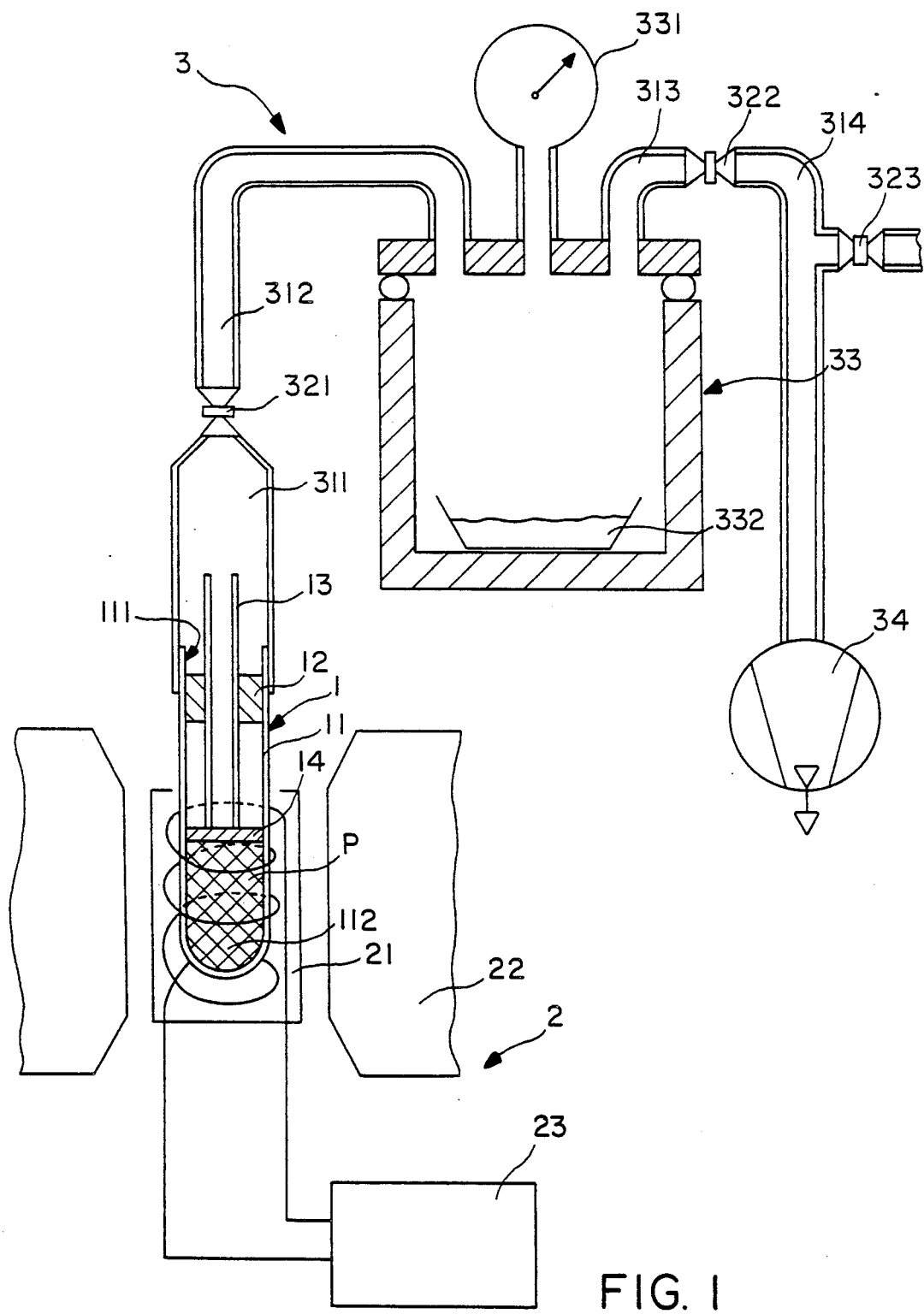
FIG. 1 is the apparatus embodiment of the present invention.

The method of the invention is performed by the apparatus of the invention, which is shown in FIG. 1 and consists of a measuring vessel 1, a NMR spectrometer 2 with coherent pulses and a vacuum pump system 3.

The measuring vessel 1 consists of a tubular cylinder 11, in which near to its orifice 111 a centring ring 12 is tightly inserted. A supporting tube 13 is in a tight fit conducted through the centring ring 12. A cover 14, which is permeable for the impregnating agent vapor, is leaned against the end of the supporting tube 13, which is directed towards the measuring vessel bottom 112. The cover 14 on its circumference tightly fits the inner wall of the cylinder 11. The cylinder 11 and the supporting tube 13 are preferably made of glass, the permeable cover 14, however, is preferably made of a glass fibre layer.

A vacuum pipe 311 of the vacuum pump system 3 is tightly connected to the cylinder 11. The vacuum pipe 311 is further connected to a vacuum vessel 33 through a valve 321 and through a vacuum pipe 312. The vacuum vessel 33 is preferably provided with a vacuum gauge 331 and, additionally, with a desiccator 332. Through vacuum pipes 313, 314, which are mutually connected through a valve 323, the vacuum vessel is connected to a vacuum pump 34. Through the valve 323 the vacuum pipe 313 may be put in contact with the atmosphere. As the vacuum pump 34 preferably a rotary pump is used.

The measuring vessel 1 with the specimen P is put into a thermostatically controlled probe 21 of the NMR spectrometer 2. The probe 21 is connected to rf supply and display circuit 23 of the spectrometer 2 and is placed between spectrometer pole pieces 22.

The specimen P, whose examined substance is impregnated as it is described in the Prior Art section, is placed into the tubular cylinder 11 of the measuring vessel 1 and is covered by the permeable cover 14, which is fastened opposite the measuring vessel 1. The surface of the cover 14 must be much smaller than the surface of the examined substance that has to be determined. The vacuum pump 34 generates a vacuum of about 1 mbar, that is below the saturated vapor pressure of the impregnating agent. The cover 14 prevents lumps to be stripped off the specimen P when the vacuum pump 34 is started. For the same reason at this moment the sucking effect of the vacuum pump 34 is reduced by a suitable opening of the valve 323.

Figure 2:
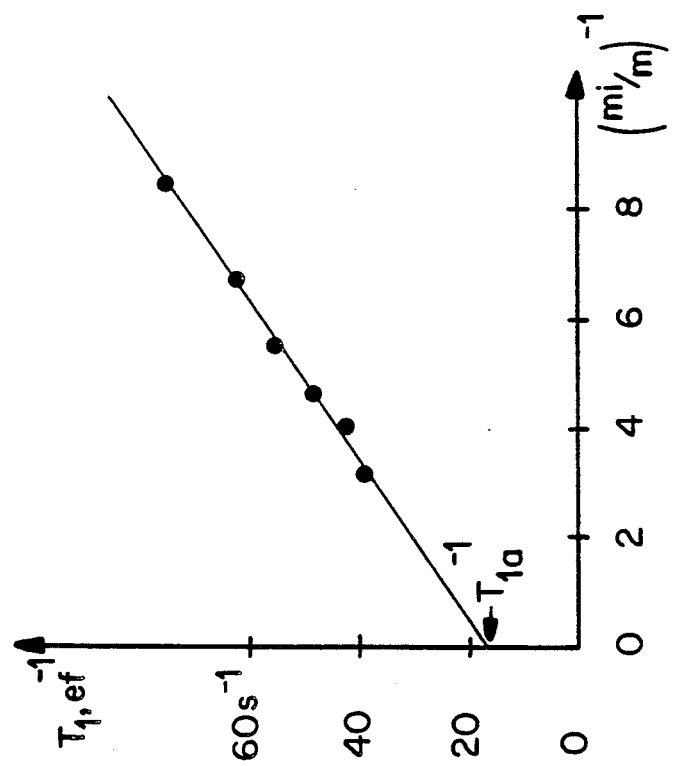
FIG. 2 is a graph representing the reciprocal effective relaxation time $T_{1,ef}$ vs. the reciprocal impregnation level $m_i/m$ for an examined substance.

The impregnating agent evaporates from the specimen P and is rapidly removed. At the same time the NMR signal of the free precession of the impregnating agent protons is observed. The removal of the impregnating agent is interrupted at several intensity values I of this signal according to a previously obtained calibration graph I vs. $m_i/m$, which values are situated within the linearly shaped part of the graph $T_{1,ef}^{-1}$ vs. $(m_i/m)^{-1}$ (FIG. 2). The spin-lattice relaxation rate of the impregnating agent protons is measured at impregnation levels $m_i/m$ corresponding to the intensity values I. Some impregnating agent molecules are adsorbed on the surface of the examined substance, other molecules, however, are not influenced by the substance and they behave like in a specimen of the pure impregnating agent. Since there exists an interchange of impregnating agent molecules between the two phases, the effective relaxation time is measured depending on the relative number of impregnating agent molecules within each phase.

The specific surface $s_{NMR}$ is calculated from the equation:

$$s_{NMR} = A \left( \frac{1}{T_{1b}} - \frac{1}{T_{1a}} \right)^{-1} \cdot \frac{T_{1,ef}^{-1}}{\left( \frac{m_i}{m} \right)^{-1}}$$

Herein the relaxation time $T_{1f}$ is determined as a valve to which the effective relaxation time $T_{1,ef}$ approaches at continuing the evaporation. The parameters $T_{1a}$ and $\Delta T_{1,ef}^{-1}/\Delta(m_i/m)^{-1}$ are determined from the graph $T_{1,ef}^{-1}$ vs. $(m_i/m)^{-1}$ in FIG. 2 as the ordinate axis intercept and as the slope of the line, respectively. By A the specimen surface is represented which is covered by molecules comprised in 1 gram of the impregnating agent.

The resolution power of the spectrometer 2 should be good enough to observe the behaviour of the impregnating agent protons within the pores of the examined substance even up to the formation of a monomolecular layer adsorbed on the pore walls. The sum of the $\pi/2$ pulse duration and of the dead time should be one order of magnitude lower than the duration of the free precession signal.

An advantage of the method according to the invention resides above all in that it is considerably faster than the known method, since at the pressure below the saturated vapor pressure of the impregnating agent the impregnation level of the specimen is quickly reduced, whereas it is prevented that lumps were stripped off the specimen in the case of an examined powdery substance.

The accuracy of the proposed method is higher than the accuracy of the known method since by the low pressure around the specimen there is prevented the condensation of the impregnating agent on the walls of the measuring vessels and the impregnating agent is more uniformly distributed within the specimen.

A further advantage resides in that the method of the invention is also suitable for determining the specific surface of substances of this kind, for which substances, besides the relaxation rate of the protons in the adsorbed impregnating agent layer, there has to be taken into account the relaxation rate of the protons in the "in situ" volume of the impregnating agent.

When solving the given problem concerning the apparatus the invention actually makes use of means that are separately known. The value of the invention, however, is not reduced by this fact since by functionally joining together these means a specially advantageous functioning is achieved, for example, the observation of the time development of the surface of the specimen by the apparatus according to the invention.

EXAMPLE OF EMBODIMENT I

A speciment with the impregnation level $m_i/m = 0.32$ was prepared by mixing industrially ground cement PCP (Salonit Anhovo, 4.6. 1987) and distilled water for 2 minutes. The speciment with a mass of 1.3 g was placed in the measuring vessel 1 and covered by the permeable cover 14, which was made of a layer (with a thickness of 1 mm and a weight of 0.2 g) of Owens Corning glass fibres with the specific surface $s_{NMR} = 50$ m²/g.

The measurements were performed at room temperature; the resonance frequency 46 MHz was applied in the NMR spectrometer 2 with two $\pi/2$ pulses and with a varying time interval between both pulses. The intensity of the free precession signals was measured 15 μs after the $\pi/2$ pulses. After the initial effective relaxation time $T_{1,ef}$ was measured, the pressure in the measuring vessel 1, which had been inserted into the probe 21 of the NMR spectrometer 2, was reduced to 10 mbar. The water evaporation began.

The intensity I of the NMR signal was observed and at determined intensity values the measuring vessel was detached from the vacuum pump system 3. Each time the impregnation level $m_i/m$ was determined by weighing and the corresponding effective relaxation time $T_{1,ef}$ was measured (FIG. 2):

| I | $(m_i/m)^{-1}$ | $T_{1,ef}^{-1}$ |
|---|---|---|
| 5.0 | 3.13 | 40 s$^{-1}$ |
| 4.0 | 4.00 | 43 |
| 2.5 | 4.60 | 49 |
| 1.8 | 5.50 | 56 |
| 1.3 | 6.70 | 63 |

From the graph in FIG. 2 the slope of the straight line was determined:

$$\frac{\Delta(T_{1,ef}^{-1})}{\Delta\left(\frac{m_i}{m}\right)^{-1}} = 7.0\,(1 \pm 0.02)\,s^{-1},$$

$$\frac{1}{T_{1a}} = 17\,s^{-1}$$

(for non-adsorbed water $1/T_{1a} = 1.4\,s^{-1}$).

Figure 3:
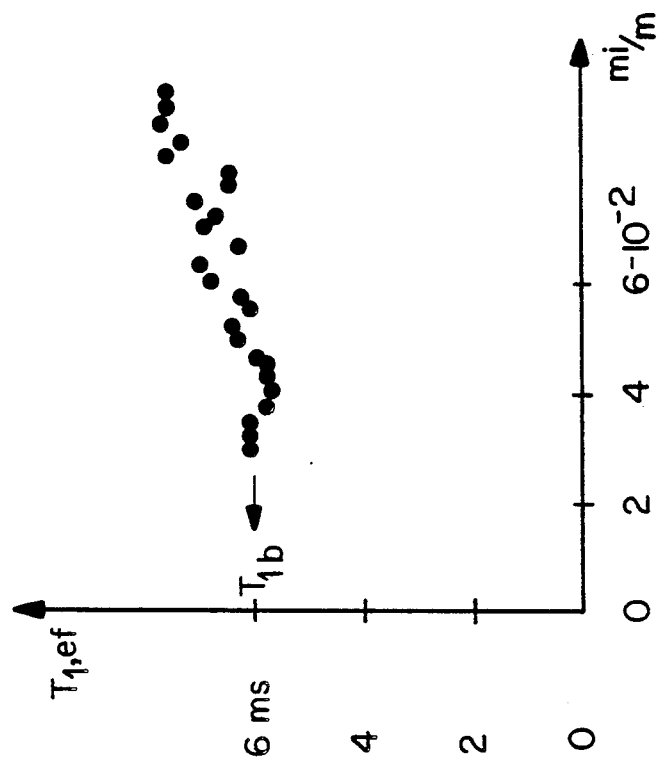
FIG. 3 is a graph of the effective relaxation time $T_{1,ef}$ vs. impregnation level $m_i/m$.

Afterwards the effective relaxation times $T_{1,ef}$, which were approaching the relaxation time $T_{1b}$ (FIG. 3) were measured at strongly reduced impregnation levels $m_i/m$ of the specimen while the water evaporation continued: 7.6 ms, 7.6 ms, 7.7 ms, 7.3 ms, 7.6 ms, 6.5 ms, 6.5 ms, 7.1 ms, 6.7 ms, 6.9 ms, 6.3 ms, 7.0 ms, 6.8 ms, 6.3 ms, 6.1 ms, 6.4 ms, 6.3 ms, 6.0 ms, 5.8 ms, 5.8 ms, 5.7 ms, 5.8 ms, 6.1 ms, 6.1 ms, 6.1 ms.

This measurement of the effective relaxation time $T_{1,ef}$ was performed within less than 20 minutes as soon as the correlation coefficient $r^2$ began to sink below 0.99 because of the continuing evaporation and because of the intensity decrease due to the slow cement hydratization. The result of this measurement was:

$$T_{1b} = 6.0\,(1 \pm 0.05)\,ms.$$

From the expression for the determination of the specific surface $s_{NMR}$, the specific surface of the industrially ground cement PCP was calculated:

$$s_{NMR} = 175\,(1 \pm 0.07)\,m^2/g.$$

The complete method took 90 minutes. Therefore the measurements needed to determine the specific surface of the cement were performed during the state of quiescence with respect to the hydratization of the cement.

EXAMPLE OF EMBODIMENT II

A specimen with the impregnation level $m_i/m = 0.16$ was prepared in vacuum by impregnating a piece crumbled away from a clay modular block with water. After that the method was performed as in Example I. The specific surface of the examined modular block was determined to be $$s_{NMR} = 310\,(1 \pm 0.07)\,m^2/g.$$

EXAMPLE OF EMBODIMENT III

A specimen with the impregnation level $m_i/m = 0.20$ was prepared by mixing tricalcium silicate hand-ground in a mortar (with admixture of 3 wt. %.Fe$_2$O$_3$) and ethanol. As in Example I there were determined $$\frac{\Delta(T_{1,ef}^{-1})}{\Delta\left(\frac{m_i}{m}\right)^{-1}} = 0.043\,(1 \pm 0.01)\,s^{-1},$$

$$\frac{1}{T_{1a}} = 0.65\,s^{-1}.$$

With seven subsequent measured values $T_{1,ef}$ the relaxation time $T_{1b} = 130\,(1 \pm 0.06)$ ms was determined within 5 minutes while the ethanol vapor was removed by 100 g silicagel placed in the desiccator 332.

The specific surface of the examined substance was determined:

$$s_{NMR} = 15\,(1 \pm 0.07)\,m^2/g.$$

What is claimed is:

1. A method for determining the specific surface of a porous or powdery substance by measuring the spin-lattice relaxation rate of impregnating agent protons, wherein from a specimen P, which is impregnated to the impregnation level $m_i/m$ by an impregnating agent which is neither allowed to react chemically with the examined substance nor to get occluded by it, the impregnating agent is removed and with a NMR spectrometer applying coherent pulses at several impregnation level values $m_i/m$ the effective spin-lattice relaxation time $T_{1,ef}$ of the exchanging impregnating agent protons is measured, said method further including the steps of:

removing the impregnating agent from the specimen (P) by evaporation at a reduced pressure around the specimen (P) wherein said reduced pressure is below the saturated vapor pressure of the impregnating agent;

observing the intensity I of the spectrometer signal and interrupting the removal of the impregnating agent at several intensity values I according to a previously obtained calibration graph I vs. $m_i/m$, wherein said calibration graph intensity values I are situated within the linear part of the plot of $T_{1,ef}^{-1}$ vs. $(m_i/m)^{-1}$;

determining level $m_i/m$ by weighing the sample and measuring the relaxation time $T_{1,ef}$ before starting the removal of the impregnating agent and after each interrupting of the removal of the impregnation;

determining a relaxation time $T_{1b}$ which the relaxation time $T_{1,ef}$ approaches at continuing evaporation; and calculating the specific surface $s_{NMR}$ from the following equation:

$$s_{NMR} = A\left(\frac{1}{T_{1b}} - \frac{1}{T_{1a}}\right)^{-1} \cdot \frac{\Delta T_{1,ef}^{-1}}{\Delta\left(\frac{m_i}{m}\right)^{-1}}$$

wherein A is the surface covered by the molecules comprised in 1 g of the impregnating agent, and from the graph $T_{1,ef}^{-1}$ vs. $(m_i/m)^{-1}$ the ordinate axis intercept $T_{1a}$ and the slope $\Delta T_{1,ef}^{-1}/\Delta(m_i/m)^{-1}$ of the line are determined.

2. A method according to claim 1, wherein the specimen (P) is thermostatically controlled during the removal of the impregnating agent and the measurement of the relaxation time $T_{1,ef}$.

3. A method according to claim 2, wherein the specimen (P) is covered by a permeable cover which is fixed with respect to a measuring vessel and whose surface is much smaller than the surface of the examined substance.

4. A method according to claim 3, wherein the pressure in a vacuum pump system, which is provided for removal of the impregnating agent, is reduced at a predetermined low speed by a valve connected to the atmosphere, such as to prevent lumps from being stripped from the specimen.

5. A method according to claim 3, wherein the impregnating agent is removed to a desiccator which is placed in a vacuum vessel of a vacuum pump system.

6. A method according to claim 4, wherein the impregnating agent is removed to a desiccator which is placed in a vacuum vessel of the vacuum pump system.

* * * * *

UNITED STATES PATENT AND TRADEMARK OFFICE
CERTIFICATE OF CORRECTION

PATENT NO. : 5,096,826
DATED : March 17, 1992
INVENTOR(S) : Lenart Barbic, et al.

It is certified that error appears in the above-identified patent and that said Letters Patent is hereby corrected as shown below:

Title page:
Item (75) delete "Magda Godina".

Signed and Sealed this

Twenty-eighth Day of April, 1992

Attest:

HARRY F. MANBECK, JR.

Attesting Officer

Commissioner of Patents and Trademarks